US007295692B2

United States Patent
Nay et al.

(10) Patent No.: US 7,295,692 B2
(45) Date of Patent: Nov. 13, 2007

(54) PROCESS AND APPARATUS FOR DETECTION OF THE CARDIAC CYCLE

(75) Inventors: Maria-Magdalena Nay, Cachan (FR); Christophe Blondel, Nice (FR); Laurence Gavit, Paris (FR); Régis Vaillant, Villebon sur Yvette (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 636 days.

(21) Appl. No.: 10/727,270

(22) Filed: Dec. 3, 2003

(65) Prior Publication Data
    US 2005/0002549 A1    Jan. 6, 2005

(30) Foreign Application Priority Data
    Dec. 6, 2002 (FR) ................... 02 15443

(51) Int. Cl.
    *G06K 9/00* (2006.01)
(52) U.S. Cl. ............ 382/131; 382/103; 382/107; 600/479; 600/513
(58) Field of Classification Search ............ 382/103, 382/107, 128, 131, 132, 286, 308; 600/479, 600/481, 513
    See application file for complete search history.

(56) References Cited

U.S. PATENT DOCUMENTS

| 5,533,085 | A | * | 7/1996 | Sheehan et al. | ............ 378/95 |
| 6,252,924 | B1 | | 6/2001 | Woodford et al. | |
| 6,426,987 | B2 | * | 7/2002 | Nakamura et al. | ............ 378/4 |
| 6,554,774 | B1 | * | 4/2003 | Miele | ............ 600/485 |
| 7,031,504 | B1 | * | 4/2006 | Argiro et al. | ............ 382/131 |
| 2007/0036417 | A1 | * | 2/2007 | Argiro et al. | ............ 382/131 |

FOREIGN PATENT DOCUMENTS

WO    WO 02 26125 A    4/2002

OTHER PUBLICATIONS

Corney et al, "Cyclic Flow Patterns in Human Cornary Arteries", Computers in Cardiology 2001, Sep. 23-26, 2001 pp. 21-24.*

* cited by examiner

*Primary Examiner*—Bhavesh M Mehta
*Assistant Examiner*—Christopher Lavin
(74) *Attorney, Agent, or Firm*—Cantor Colburn LLP (57) ABSTRACT

A process for cardiac movements to be used with a radiography apparatus (1) wherein acquiring of a series of successive images $I_n$ of the region of the heart, an analysis of at least some of the images thus acquired to identify a heart movement; and a determination of the cardiac cycle starting from this movement.

26 Claims, 4 Drawing Sheets

FIG_4

PROCESS AND APPARATUS FOR DETECTION OF THE CARDIAC CYCLE

CROSS-REFERENCE TO RELATED APPLICATIONS

This application claims a benefit of a priority under 35 USC 119(a)-(d) to FR 02 15443 filed Dec. 6, 2002, the entire contents of which are hereby incorporated by reference.

BACKGROUND OF THE INVENTION

This invention relates to a process and an apparatus for detection of a cardiac movement or cycle of a patient. More particularly, the invention relates to the detection of the cardiac cycle starting from an angiogram of coronary vessels. Identification of cardiac movement from images of coronary arteries acquired using a radiography apparatus during selective injection of a contrast agent within these coronary arteries, can be useful in a number of algorithms:

Calculation of a myocardial perfusion index based on analysis of the variation of density in a series of images throughout different cardiac cycles.

Production of a fixed sequence, in other words a sequence with no or very few displacements of the coronary arteries between the different images making up the sequence.

Synchronization of two multi-modal sequences for the same patient, for example, one sequence acquired in fluoroscopy and another sequence acquired in conventional recording mode, the images of the two sequences possibly being combined.

Production of a three-dimensional image reconstruction by applying known reconstruction algorithms from a series of images chosen to illustrate the same instant in the cardiac cycle.

There are difficulties with these algorithms. A first difficulty is that the electrocardiogram (ECG) signal is necessary to know the instant in the cardiac cycle associated with each image acquired in the sequences. But this signal is not always directly available with the images. Furthermore, the ECG signal is an electrical signal that describes the stimulation of the heart muscle but not the effective mechanical movement of this muscle. However in the known application of algorithms, it is necessary to know the position of injected coronary arteries, in other words to know the mechanical behaviour of the heart A second difficulty is that the patient might breath during the acquisition or that the images from two different cardiac cycles may be slightly different.

BRIEF DESCRIPTION OF THE INVENTION

An embodiment of the invention provides a process for the detection of the cardiac movement capable of solving the above-mentioned difficulties. An embodiment of the invention, is a process for a cardiac movement detection designed to be implemented within a radiography apparatus of the type comprising means for providing a source of radiation, means for recording placed facing the source, and a means for support placed between the source and means for recording on which there is a patient for whom an image of a region of the heart is to be made. The process may be automatic and implemented by a suitable computer program.

An embodiment of the process comprises:
a) acquisition of a series of successive images $I_n$ of a region of a heart;
b) analysis of at least some of the images thus acquired to identify a heart movement; and
c) determination of the cardiac cycle starting from this movement.

Thus, an embodiment of the process can be used to determine the effective mechanical movement of the heart during its cycle starting from a series of images acquired by a radiography apparatus without the need for the electrocardiogram signal so that the different images can be synchronized with the electrocardiogram. Furthermore, during the calculation of integral displacements between successive images in the series of images, an embodiment of the process can evaluate minor differences that may arise between two cardiac cycles contained in the series of images.

An embodiment of the invention is a radiography apparatus of the type comprising means for providing a source of radiation, means for recording facing the source and means for support placed between the source and the means for recording on which there is a patient for whom a region of the heart is to be imaged, the radiography apparatus comprising means for implementing the process.

BRIEF DESCRIPTION OF THE DRAWINGS

Other characteristics and advantages will be better understood from the following description of an embodiment of the invention and the drawings, in which.

DETAILED DESCRIPTION OF THE INVENTION

Figure 1:
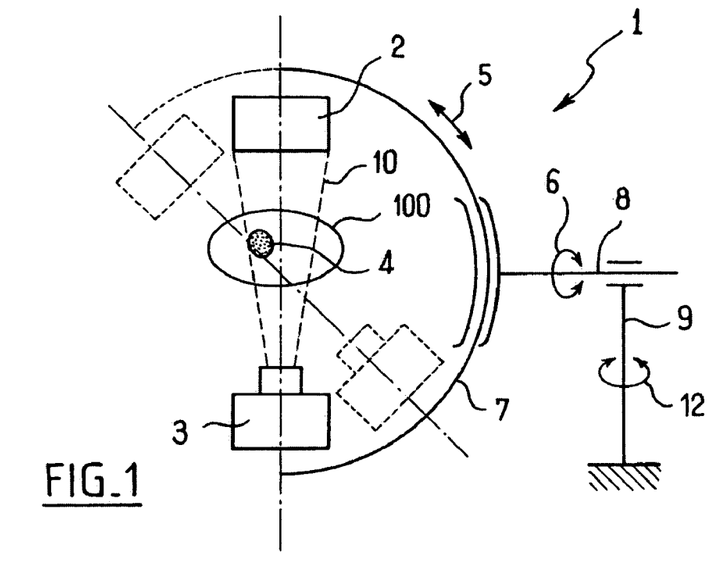
FIG. 1 is a diagrammatic view of a radiography apparatus capable of implementing the process.

With reference to FIG. 1, a radiography apparatus 1 comprises means for recording images 2 and means for providing a source of radiation 3, such as an X-ray source. The means for recording images 2 may comprise radiographic plates of a plane sensor or a luminance amplifier associated with a camera. The radiation source 3 and the means for recording images 2 are fixed to each end of a carrier arm 7 acting as a positioner, in this case in the form of a semi-circle. The semi-circular arm 7 is connected by sliding on a second arm 8. The second arm 8 is connected in rotation about an installed base 9 of the radiography apparatus 1. The base 9 is free to rotate 12 with respect to the ground.

Arm 8 is essentially capable of making rotation movements 6 about its own axis. The semi-circular arm 7 is capable of sliding with respect to the arm 8, such that the semi-circular arm 7 makes a rotation movement 5 with respect to the center of the semi-circle forming the arm 7.

During use, the body of the patient 100 is positioned between the radiation source 3 and the means for recording images 2, on a means for support (not shown) such that the heart 4 of the patient 100 is within the field 10 of the apparatus.

Figure 2:
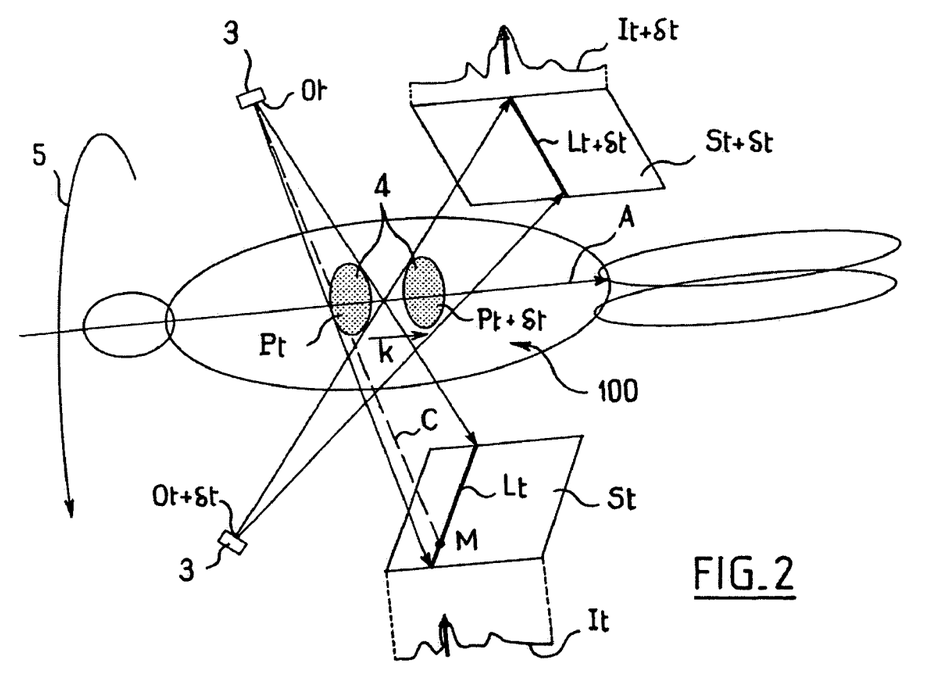
FIG. 2 is a principle diagram of the process.

With reference to FIG. 2, the patient 100 is lying down on the means for support of the radiography apparatus 1 while the radiation source 3 and the means for recording images 2 make a rotation 5 around the patient. In this case, the cranio-caudal axis of the patient 100 is approximately parallel to the axis of rotation 5 of the movement. Anatomically, during the cardiac cycle, two planes of the heart perpendicular to its cranio-caudal axis make a relative translation movement along this cranio-caudal axis associated with a rotation movement about this cranio-caudal axis. Consequently, with the patient 100 being positioned within the radiographic apparatus 1, each plane $P_t$ of the heart perpendicular to the cranio-caudal axis of the heart is projected along a line $L_t$ onto the means for recording images when this means acquires an image $S_t$.

At time t+δt, when the semi-circular arm 7 supporting the radiation source 3 and the means for recording images 2 has made a rotation movement 5 about its axis, the previously described plane $P_t$ has made a translation about the cranio-caudal axis of the heart and a rotation about this same axis and is in the position $P_{t+\delta t}$ that is then projected onto means for recording images 2 along a line $L_{t+\delta t}$ that is shown on image $S_{t+\delta t}$ acquired at this moment. The $P_t$ and $P_{t+\delta t}$ planes intersect the same types of cardiac tissues in the same proportions. Since tissues attenuate radiation passing through them by variable amounts, the sum of these attenuations along line $L_t$ is approximately equal to the sum of the attenuations along line $L_{t+\delta t}$. Thus, to determine the displacement of plane $P_t$ all that is necessary is to calculate the displacement of its projection on the means for recording images 2, in other words the displacement of line L from $L_t$ to $L_{t+\delta t}$.

Consider $R_{00}$, the intensity of the ray emitted by a radiation source 3. The image I obtained after injection of a contrast product in the coronary vessels of the heart may be modeled by:

$$I(M) = R_{00} e^{-\int c(v) \mu(x) dx - \int c(F) \mu(x) dx}$$

where C(M) is the path between the radiation source 3 modeled in FIG. 2 by point O and a point M on the image, the point M having coordinates (i,j) in pixels on the image; $\mu$ is the local attenuation coefficient along the path C that depends on the nature of tissues passed through and the wavelength of the X-rays used; V represents all points on the image belonging to the projected vessels through which the radiation passes; and F represents all points belonging to other tissues projected on the image.

If the image were not injected, the contributions of points that are not in vessels would be obtained, in other words an image $I_0$ that would be modelled as:

$$I_0(M) = R_{00} e^{-\int c(F) \mu(x) dx}$$

Consequently, the principle of the process is based on the fact that $\int c(F) \mu(x) dx$ is conserved. This entity is calculated from different images in a series of images and the vertical displacement of the heart between two successive images in the series of images is then determined.

Figure 3:
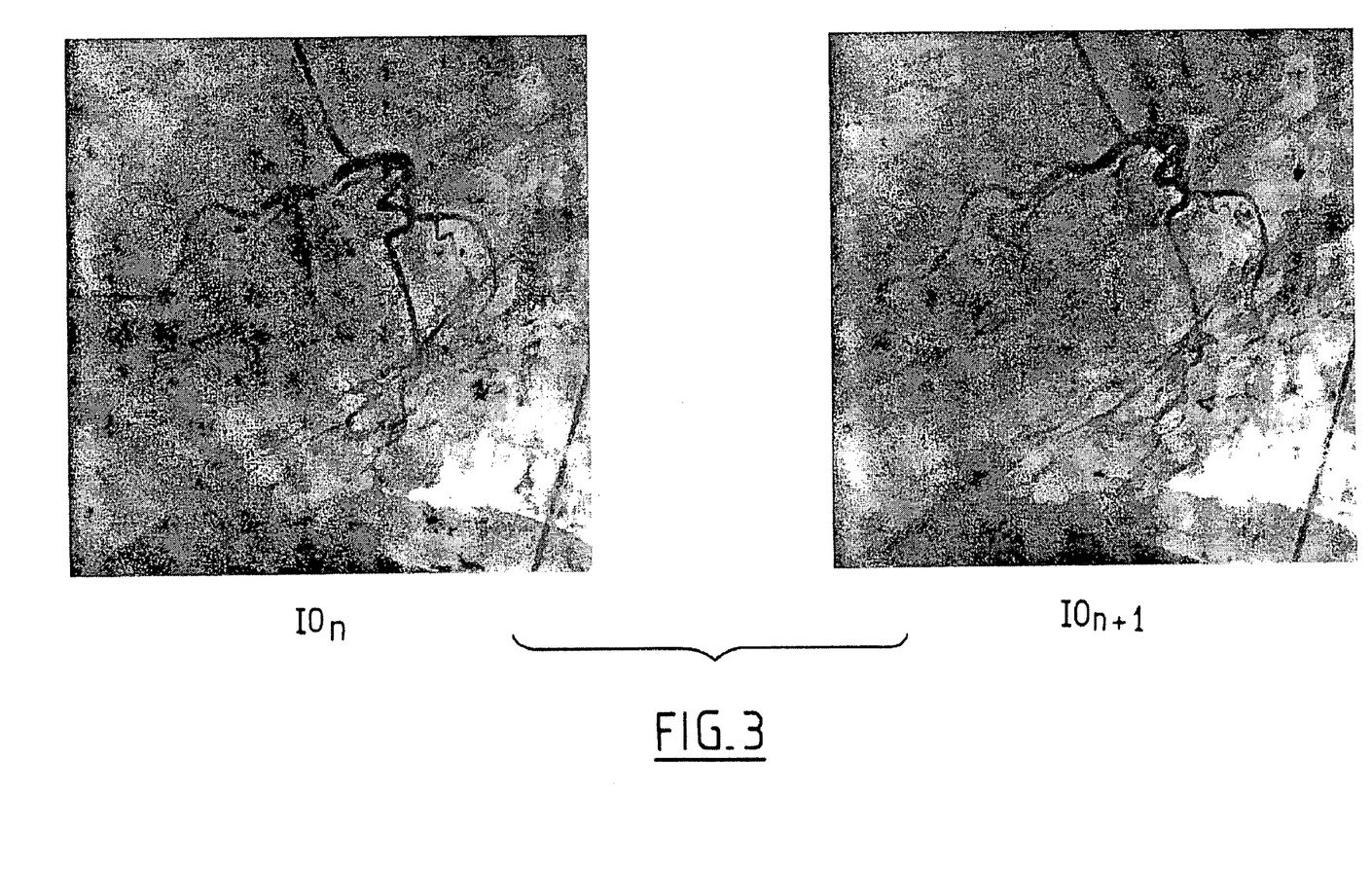
FIG. 3 shows two successive images acquired during the process.
Figure 4:
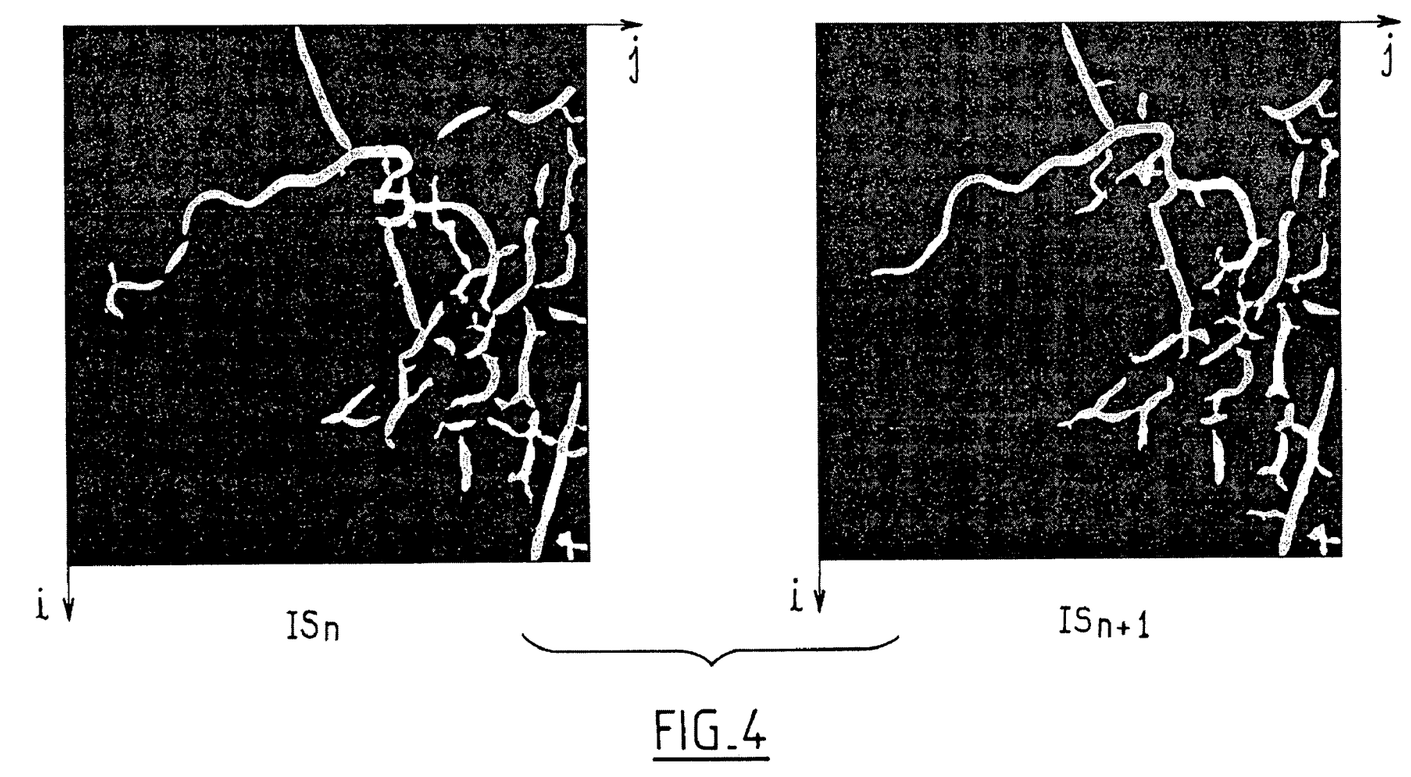
FIG. 4 is the transformation of the images in FIG. 3 into segmented images.

In one embodiment, the images acquired by the means for acquisition, i.e., the radiographic plates 2, are images of the type as shown in FIG. 3. In FIG. 3 an image $IO_n$ and the next image $IO_{n+1}$ in the series, on which the later images are visible and dark due to the injection of contrast products into the coronary vessels. The first step in the process, knowing the maximum dimensions of the arteries to be extracted, in other words a diameter of the coronary arteries, is to apply a closing mask to the initial images $IO_n$ as illustrated in FIG. 3. This closing mask may bring out structuring elements with a size equivalent to the dimensions of the arteries to be extracted and determined in advance. Application of this type of mask involves calculating a subtracted image obtained by subtraction of the closing mask from the corresponding previously calculated initial image. However, this operation does not eliminate all parasite structures present in the image. In order to achieve this, the process applies adaptive thresholding to the subtracted image by calculating a threshold so as to keep about 15% of the pixels. This assumption is based on the fact that the coronary vessels that contain a contrast product when the images are acquired give the greatest contrast. The result is a thresholded contrast image like that illustrated in FIG. 4 in which the image $IS_n$ is the thresholded image of the original image $IO_n$, and similarly, the thresholded image $IS_{n+1}$ is the thresholded image of the original image $IO_{n+1}$.

In a second step, the process determines the linear integrals $f_{IS_u}$ of the different thresholded images $IS_n$, pixel line i by pixel line i (in this case these pixel lines are perpendicular to the cranio-caudal axis of the heart), according to the formula:

$$f_{IS_u}(i) = \sum_{j=0}^{No.\ of\ columns} ln \frac{I(i,j)}{I_0(i;j)}.$$

Figure 5:
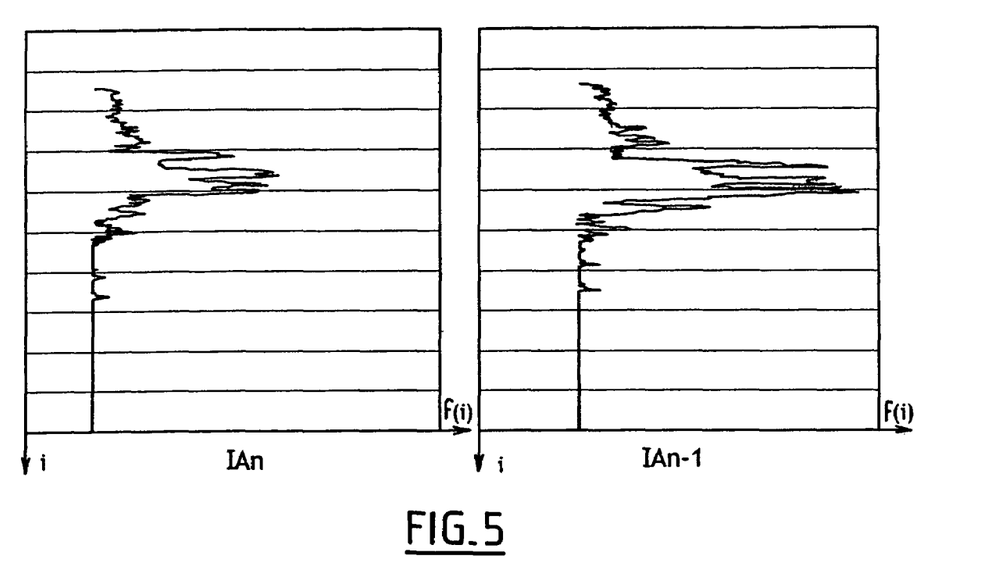
FIG. 5 is a diagram representing the attenuation coefficients calculated using the process for the images in FIG. 4.

The result is that i values of linear integrals $f_{IS_n}$ illustrated in FIG. 5 are obtained for each image $IS_n$, where $IA_n$ is the set of linear integrals associated with the image $IS_n$ and $IA_{n+1}$ is the set of linear integrals associated with the image $IS_{n+1}$.

In the next step, the process calculates an integral displacement on a sequence of images starting from all previously calculated linear integrals $IA_n$ and associated with each original image $IO_n$. The calculation of the integral displacement on a sequence of images determines the effective mechanical movement of the heart, or at least determines the variation of the translation of the different planes perpendicular to the cranio-caudal axis of the heart along this axis, and for which the projection of each of these planes on the images $IO_n$ is a pixel line i. In order to achieve this, the previous description indicated that the sum of the attenuation coefficients of projection points from the plane $P_t$ perpendicular to the cranio-caudal axis is conserved, in other words the values $f_{IS_n}$ of the linear integrals are conserved. The process calculates the displacement between two successive images $IO_n$ and $IO_{n+1}$ along this translation. The process then determines a displacement $k_{n,n+1}$ starting from linear integrals $IA_n$, $IA_{n+1}$ associated with each of the successive two images considered, $k_{n,n+1}$ that minimizes a cost function $F_{n,n+1}$ defined as follows:

$$F_{n,n+1}(k_{n,n+1}) = \sum_{i=0}^{No.\ of\ lines} |f_{IS_n}(i) - f_{IS_{n-1}}(i - k_{n,n+1})|$$

Figure 6:
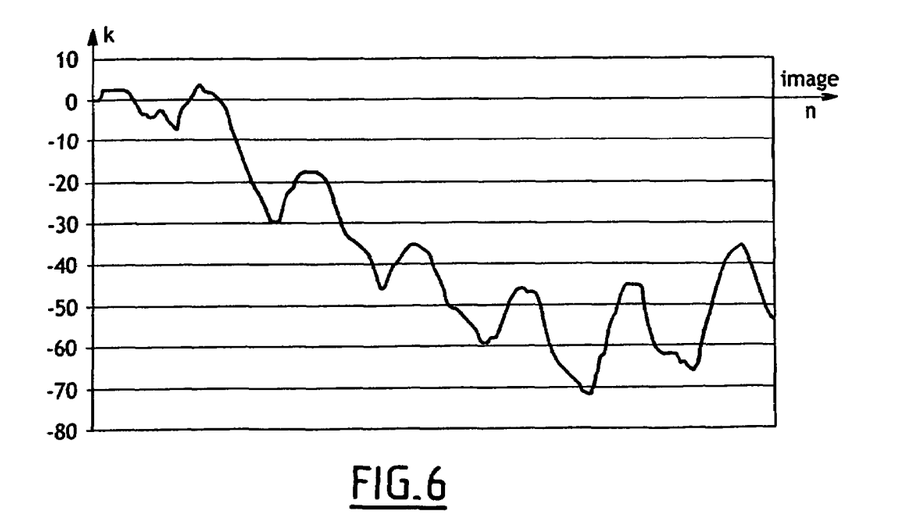
FIG. 6 is a diagram illustrating the cardiac cycle obtained using the process.

The value $k_{n,n+1}$ thus found is equal to the effective translation displacement of the heart along its cranio-caudal axis between two successive images considered. The set of values $k_{n,n+1}$ found for the entire image sequence shows the cardiac cycle as illustrated in FIG. 6.

According to an embodiment, in an additional step, the process assumes that the sequence of events is approximately the same in each cardiac cycle, and determines the synchronous images of an arbitrary origin taken from the first previously found cycle. However, in another variant embodiment for which all synchronous images to be found should enable a three-dimensional image reconstruction, images for which the contrast product is actually injected into the coronary vessels taken at the beginning of rotation of the semi-circular arm 7 of the radiography apparatus 1 should be taken into account. Different tests have shown that approximately one hundred well-injected images can be used out of a sequence containing a total of about two hundred images, and at least three synchronous images can be found among the one hundred well-injected images that can be used for three-dimensional reconstruction.

In one variant embodiment, the process calculates displacement of the heart due to the breathing movement of the patient during acquisition of the sequence of images used as input data to the process. In this step, the process is based on all previously chosen synchronous images. In a manner very similar to what was presented above, the process calculates the heart displacement due to the breathing movement. In order to illustrate this movement, it is assumed that the process uses three synchronous images $I_1$, $I_2$, $I_3$ and associated thresholded images $IS_1$, $IS_2$, $IS_3$. Starting from these three images, a cost function $F_{123}$ is defined that takes account of the fact that translation between images $I_1$ and $I_3$ is equal to the sum of the translation between images $I_1$ and $I_2$ and the translation between images $I_2$ and $I_3$, in other words $k_{13}=k_{12}+k_{23}$.

The expression of this new cost function $F_{123}$ is:

$$FI_{123}(k_{12}, k_{23}) = \sum_{i=0}^{No.\ of\ lines} \left| f_{IS_1}(i) - f_{IS_2}(i - k_{12}) \right| + \sum_{i=0}^{No.\ of\ lines} \left| f_{IS_2}(i) - f_{IS_3}(i - k_{23}) \right| + \sum_{i=0}^{No.\ of\ lines} \left| f_{IS_1}(i) - f_{IS_*}(i - k_{23}) \right|$$

Thus, the displacements $k_{12}$ between images $I_1$ and $I_2$ and $k_{23}$ between images $I_2$ and $I_3$ indicating displacements due to the breathing movements between image $I_1$ and image $I_2$ and image $I_2$ and image $I_3$ respectively, where $k_{12}$ and $K_{23}$ minimize $F_{123}$. Thus, before making a three-dimensional image reconstruction starting from synchronous images, the radiography apparatus 1 corrects these images starting from displacements due to breathing previously calculated by known image correction algorithms by translation, and then by known projection matrix correction algorithms.

Depending on the variant embodiments, the process may comprise at least one of the following characteristics:

(a) acquisition of a series of successive images $I_n$ of the region of the heart;

(b) determination of a cranio-caudal axis of the heart;

(c) for each image $I_n$, calculation of the series of images of a set of attenuation coefficients of points on the image representing vessels in the region of the heart along lines perpendicular to the cranio-caudal axis of the heart;

(d) calculation of the integral displacement $k_{n,n+1}$ between two successive images $I_n$ and $I_{n+1}$ of the series of images starting from the set of attenuation coefficients calculated for each of the two successive images; and (e) determination of the cardiac cycle starting from all previously calculated integral displacements.

The determination of a cranio-caudal axis of the heart may comprises:

(b1) for each image $I_n$ in the series of images, calculation of an associated thresholded image $IS_n$, only keeping vessels in the heart region; and (b2) determination of all attenuation coefficients for points on the image starting from thresholded images along lines perpendicular to the axis of the heart.

The calculation of the thresholded image $IS_n$ may comprises:

(b1i) determination of at least one dimension, particularly a diameter, of vessels in the heart region to be kept;

(b1ii) calculation of a closing image starting from the maximum dimension of vessels in the heart region to be kept;

(b1iii) calculation of an intermediate image by subtracting the closing image from the initial image; and (b1iv) calculation of the thresholded image by application of an appropriate thresholding on the intermediate image.

Thresholding is applied such that it keeps only about 15% of the pixels in the intermediate image;

the set of attenuation coefficients of points on image $I_n$ along line i is modeled by a linear integral $f_{I_n}(i)$ of these attenuation coefficients along this line;

the linear integral is expressed by a formula for line i, $$f_{I_n}(i) = \sum_{j=0}^{No.\ of\ clounms} ln \frac{I_n(i, j)}{I_{0n}(i, j)} \quad \text{where}$$

$$I_n(i, j) = R_{00} e^{-\int_{C(V)} \mu(x)dx - \int_{C(F)} \mu(x) dx} \quad \text{and}$$

$$I_{0n}(i, j) = R_{00} e - \int_{C(F)} \mu(x) d\,x,$$

where $R_{00}$ is the initial intensity of radiation emitted by the radiation source; C(M) is the path between the radiation source and the point M on the image $I_n$ with coordinates (i,j) in pixels on the image; μ is the local attenuation coefficient along path C that depends on the nature of the tissues crossed and the wavelength of the radiation used; V represents all points on image $I_n$ belonging to the projected vessels through which the radiation pass; and F represents all points belonging to other tissues projected onto image $I_n$.

The integral displacement $k_{n,n+1}$ between two successive images $I_n$ and $I_{n+1}$ is calculated starting from all linear integrals associated with each successive image; and the integral displacement is the value of $k_{n,n+1}$ that minimizes an $$F_{n,n+1}(k_{n,n+1}) = \sum_i | f_{I_n}(i) - f_{I_{n-1}}(i - k_{n,n+1}) |$$

type cost function.

The process may comprise an additional step (f) to choose a subset of synchronous images in the heart cycle from the series of images, starting from the previously determined cardiac cycle.

The process may also comprises a step (g) to determine an integral displacement due to breathing of the patient (100)

between synchronous images, the determination being done in the same way as in the step (c).

One skilled in the art may make or propose a modification in structure/way and/or function and/or result for the disclosed embodiments and equivalents thereof without departing from the scope and extant of the invention.

What is claimed is:

1. A process for detection of cardiac movement comprising:
    a. acquiring a series of successive images $I_n$ of the region of a heart;
    b. determination of a cranio-caudal axis of the heart;
    c. for each image $I_n$, calculation of the series of images of a set of attenuation coefficients of points on the image representing vessels in the region of the heart, the set of attenuation coefficients along lines perpendicular to the cranio-caudal axis of the heart;
    d. calculation of the integral displacement $k_{n,n+1}$ between two successive images $I_n$ and $I_{n+1}$ of the series of images starting from the set of attenuation coefficients calculated for each of the two successive images; and
    e. determination of the cardiac cycle starting from all previously calculated integral displacements.

2. The process according to claim 1 wherein step b comprises:
    b1. for each image $I_n$ in the series of images, calculation of an associated thresholded image $IS_n$, only keeping vessels in the heart region, and
    b2. determine all attenuation coefficients for points on the image starting from thresholded images along lines perpendicular to the axis of the heart.

3. The process according to claim 2 wherein the step to calculate the thresholded image $IS_n$ comprises:
    b1i. determination of at least one dimension, particularly a diameter, of vessels in the heart region to be kept;
    b1ii. calculation of a closing image starting from the maximum dimension of vessels in the heart region to be kept;
    b1iii. calculation of an intermediate image by subtracting the closing image from the initial image; and
    b1iv. calculation of the thresholded image by application of an appropriate thresholding on the intermediate image.

4. Process according to claim 3 wherein the thresholding is applied such that it keeps only about 15% of the pixels in the intermediate image.

5. The process according to claim 4 wherein the set of attenuation coefficients of points on image $I_n$ along line i is modeled by a linear integral $f_{In}(i)$ of these attenuation coefficients along this line.

6. The process according to claim 5 wherein the linear integral is expressed by a formula for line i, $$f_{In}(i) = \sum_{j=0}^{Nb.\ of\ columns} ln \frac{I_n(i,j)}{I_{0n}(i,j)} \text{ where}$$

$$I_n(i,j) = R_{00} e^{-\int_{C(V)} \mu(x) dx - \int_{C(F)} \mu(x) dx} \text{ and}$$

$$I_{0n}(i,j) = R_{00} e - \int_{C(F)} \mu(x) dx,$$

where:
    $R_{00}$ is the initial intensity of radiation;
    C (M) is the path between a radiation source and a point M on an image $I_n$ with coordinates (i,j) in pixels on the image;
    $\mu$ is the local attenuation coefficient along path C (M) that depends on the nature of the tissues crossed and the wavelength of the radiation used;
    V represents all points on image $I_n$ belonging to the projected vessels through which the radiation pass; and
    F represents all points belonging to other tissues projected onto image $I_n$.

7. The process according to claim 5 wherein the integral displacement $k_{n,n+1}$ between two successive images $I_n$ and $I_{n+1}$ is calculated starting from all linear integrals associated with each successive image.

8. The process according to claim 5 wherein the integral displacement is the value $k_{n,n+1}$ that minimizes an $$F_{n,n+1}(k_{n,n+1}) = \sum_i |f_{I_n}(i) - f_{I_{n-1}}(i - k_{n,n+1})|$$

type cost function.

9. The process according to claim 3 wherein the set of attenuation coefficients of points on image $I_n$ along line i is modeled by a linear integral $f_{In}(i)$ of these attenuation coefficients along this line.

10. The process according to claim 9 wherein the linear integral is expressed by a formula for line i, $$f_{In}(i) = \sum_{j=0}^{Nb.\ of\ columns} ln \frac{I_n(i,j)}{I_{0n}(i,j)} \text{ where}$$

$$I_n(i,j) = R_{00} e^{-\int_{C(V)} \mu(x) dx - \int_{C(F)} \mu(x) dx} \text{ and}$$

$$I_{0n}(i,j) = R_{00} e - \int_{C(F)} \mu(x) dx,$$

where:
    $R_{00}$ is the initial intensity of radiation;
    C (M) is the path between a radiation source and a point M on an image $I_n$ with coordinates (i,j) in pixels on the image;
    $\mu$ is the local attenuation coefficient along path C (M) that depends on the nature of the tissues crossed and the wavelength of the radiation used;
    V represents all points on image $I_n$ belonging to the projected vessels through which the radiation pass; and
    F represents all points belonging to other tissues projected onto image $I_n$.

11. The process according to claim 9 wherein the integral displacement $k_{n,n+1}$ between two successive images $I_n$ and $I_{n+1}$ is calculated starting from all linear integrals associated with each successive image.

12. The process according to claim 9 wherein the integral displacement is the value of $k_{n,n+1}$ that minimizes an $$F_{n,n+1}(k_{n,n+1}) = \sum_i |f_{I_n}(i) - f_{I_{n-1}}(i - k_{n,n+1})|$$

type cost function.

13. The process according to claim 2 wherein the set of attenuation coefficients of points on image $I_n$ along line i is modeled by a linear integral $f_{In}(i)$ of these attenuation coefficients along this line.

14. The process according to claim 13 wherein the linear integral is expressed by a formula for line i, $$f_{In}(i) = \sum_{j=0}^{Nb.\ of\ columns} ln \frac{I_n(i,j)}{I_{0n}(i,j)} \text{ where}$$

$$I_n(i,j) = R_{00} e^{-\int_{C(V)} \mu(x)dx - \int_{C(F)} \mu(x)dx} \text{ and}$$

$$I_{0n}(i,j) = R_{00} e^{-\int_{C(F)} \mu(x)dx},$$

where:
- $R_{00}$ is the initial intensity of radiation;
- C (M) is the path between a radiation source and a point M on an image $I_n$ with coordinates (i,j) in pixels on the image;
- μ is the local attenuation coefficient along path C (M) that depends on the nature of the tissues crossed and the wavelength of the radiation used;
- V represents all points on image $I_n$ belonging to the projected vessels through which the radiation pass; and
- F represents all points belonging to other tissues projected onto image $I_n$.

15. The process according to claim 13 wherein the integral displacement $k_{n,n+1}$ between two successive images $I_n$ and $I_{n+1}$ is calculated stating from all liner integrals associated with each successive image.

16. The process according to claim 13 wherein the integral displacement is the value of $k_{n,n+1}$ that minimizes an $$F_{n,n+1}(k_{n,n+1}) = \sum_i |f_{I_n}(i) - f_{I_{n-1}}(i - k_{n,n+1})|$$

type cost function.

17. The process according to claim 1 wherein the set of attenuation coefficients of points on image $I_n$ along line i is modeled by a linear integral $f_{In}(i)$ of these attenuation coefficients along this line.

18. The process according to claim 17 wherein the linear integral is expressed by a formula for line i, $$f_{In}(i) = \sum_{j=0}^{Nb.\ of\ columns} ln \frac{I_n(i,j)}{I_{0n}(i,j)} \text{ where}$$

$$I_n(i,j) = R_{00} e^{-\int_{C(V)} \mu(x)dx - \int_{C(F)} \mu(x)dx} \text{ and}$$

$$I_{0n}(i,j) = R_{00} e^{-\int_{C(F)} \mu(x)dx},$$

where:
- $R_{00}$ is the initial intensity of radiation;
- C(M) is the pat between a radiation source and a point M on an image $I_n$ with coordinates (i,j) in pixels on the image;
- μ is the local attenuation coefficient along path C (M) that depends on the nature of the tissues crossed and the wavelength of the radiation used;
- V represents all points on image $I_n$ belonging to the projected vessels through which the radiation pass; and
- F represents all points belonging to other tissues projected onto image $I_n$.

19. The process according to claim 18 wherein the integral displacement $k_{n,n+1}$ between two successive images $I_n$ and $I_{n+1}$ is calculated starting from all linear integrals associated with each successive image.

20. The process according to claim 18 wherein the integral displacement is the value of $k_{n,n+1}$ that minimizes an $$F_{n,n+1}(k_{n,n+1}) = \sum_i |f_{I_n}(i) - f_{I_{n-1}}(i - k_{n,n+1})|$$

type cost function.

21. The process according to claim 17 wherein the integral displacement $k_{n,n+1}$ between two successive images $I_n$ and is calculated starting from all linear integrals associated with each successive image.

22. The process according to claim 21 wherein the integral displacement is the value of $k_{n,n+1}$ that minimizes an $$F_{n,n+1}(k_{n,n+1}) = \sum_i |f_{I_n}(i) - f_{I_{n-1}}(i - k_{n,n+1})|$$

type cost function.

23. The process according to claim 1 comprising:
f. choose a subset of synchronous images in the heart cycle from the series of images, starting from the previously determined cardiac cycle.

24. The process according to claim 23 comprising:
g. determine an integral displacement due to breathing of a patient between synchronous images, the determination being done in the same way as in step c.

25. A radiography apparatus comprising:
a source of radiation;
an image recorder facing the source; and
means for support placed between the source and the image recorder on which there is a patient for whom a region of a heart is to be imaged,
wherein the radiography apparatus comprises means for implementing the process of claim 1.

26. An article of manufacture for use with a computer system, the article of manufacture comprising a computer readable medium having computer readable program code means embodied in the medium, the program code means comprising:
a. computer readable program code means embodied in the medium for causing a computer to provide acquiring a series of successive images $I_n$ of the region of a heart;
b. computer readable program code means embodied in the medium for causing a computer to provide determination of a cranio-caudal axis of the heart:
c. computer readable program code means embodied in the medium for causing a computer to provide for each image $I_n$, calculation of the series of images of a set of attenuation coefficients of points on the image representing vessels in the region of the heart, the set of attenuation coefficients along lines perpendicular to the cranio-caudal axis of the heart:

d. calculation of the integral displacement $k_{n,n+1}$ between two successive images $I_n$ and $I_{n,n+1}$ of the series of images starting from the set of attenuation coefficients calculated for each of the two successive images: and e. determination of the cardiac cycle starting from all previously calculated integral displacements.

* * * * *